United States Patent
Yamada

(10) Patent No.: US 10,624,343 B2
(45) Date of Patent: Apr. 21, 2020

(54) PHENYL UREA COMPOUND, AND USE THEREOF

(71) Applicant: Sumitomo Chemical Company, Limited, Tokyo (JP)

(72) Inventor: Shinya Yamada, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/328,010

(22) PCT Filed: Aug. 24, 2017

(86) PCT No.: PCT/JP2017/030246
§ 371 (c)(1),
(2) Date: Feb. 25, 2019

(87) PCT Pub. No.: WO2018/038188
PCT Pub. Date: Mar. 1, 2018

(65) Prior Publication Data
US 2019/0223435 A1    Jul. 25, 2019

(30) Foreign Application Priority Data
Aug. 26, 2016   (JP) ................ 2016-165422

(51) Int. Cl.
  *A01N 43/34*   (2006.01)
  *A01N 43/40*   (2006.01)
  *C07D 213/69*  (2006.01)
  *A01N 47/30*   (2006.01)

(52) U.S. Cl.
  CPC ........... *A01N 43/40* (2013.01); *A01N 47/30* (2013.01); *C07D 213/69* (2013.01)

(58) Field of Classification Search
  CPC .................................. A01N 43/34
  See application file for complete search history.

(56) References Cited

U.S. PATENT DOCUMENTS

| 4,376,646 A | 3/1983 | Rohr et al. |
| 2002/0161224 A1 | 10/2002 | Pulman et al. |
| 2003/0008884 A1 | 1/2003 | Gerusz et al. |
| 2019/0174762 A1* | 6/2019 | Yamada .............. C07D 213/69 |
| 2019/0202787 A1* | 7/2019 | Yamada .............. A01N 47/34 |

FOREIGN PATENT DOCUMENTS

| EP | 1122244 B1 | 9/2004 |
| JP | S56147759 A | 11/1981 |
| JP | S60142958 A | 7/1985 |
| JP | 2001519783 A | 10/2001 |
| JP | 2002155061 A | 5/2002 |
| WO | 2006065479 A2 | 6/2006 |
| WO | 2007088996 A1 | 8/2007 |
| WO | WO-2018038189 A1 * | 3/2018 ............ A01N 47/34 |

OTHER PUBLICATIONS

English Translation of International Search Report dated Oct. 10, 2017 in International Application No. PCT/JP2017/030246.
English Translation of International Preliminary Report on Patentability dated Feb. 26, 2019 in International Application No. PCT/JP2017/030246.

* cited by examiner

*Primary Examiner* — Noble E Jarrell
*Assistant Examiner* — John S Kenyon
(74) *Attorney, Agent, or Firm* — Panitch Schwarze Belisario & Nadel LLP

(57) ABSTRACT

A compound represented by formula (1) is described:

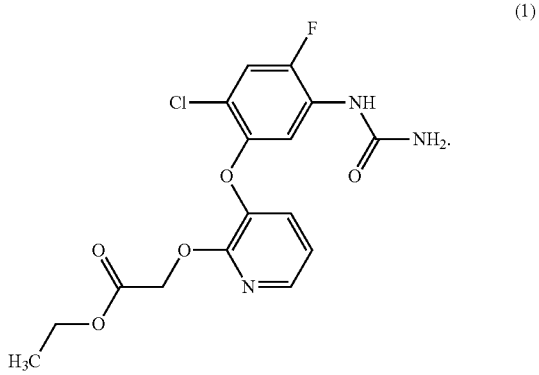

The compound has an excellent efficacy for controlling plant diseases, and is thus useful as an active ingredient for an agent for controlling plant diseases.

3 Claims, No Drawings

PHENYL UREA COMPOUND, AND USE THEREOF

CROSS-REFERENCE TO RELATED APPLICATION

This application is a Section 371 of International Application No. PCT/JP2017/030246, filed Aug. 24, 2017, which was published in the Japanese language on Mar. 1, 2018, under International Publication No. WO 2018/038188 A1, which claims priority under 35 U.S.C. § 119(b) to Japanese Application No. 2016-165422 filed on Aug. 26, 2016, the disclosures of which are incorporated herein by reference in their entireties.

TECHNICAL FIELD

The present invention is related to a phenylurea compound and a use of the same.

BACKGROUND ART

Patent document 1 describes N-[4-chloro-2-fluoro-5-{2-(ethoxycarbonyl)methoxy-3-pyridyloxy}phenyl]acetamide.

CITATION LIST

Patent Document

Patent Document 1: EP patent No. 1122244 B2

SUMMARY OF THE INVENTION

Problems to be Solved by Invention

An object of the present invention is to provide a compound having an excellent efficacy for controlling plant diseases.

Means to Solve Problems

The present inventor has intensively studied to find out a compound having an excellent control efficacy on plant diseases. As a result, he found cut that a compound represented by the following formula (1) has an excellent control efficacy on plant diseases.

That is, the present invention includes the followings.
[1] A compound represented by formula (1):

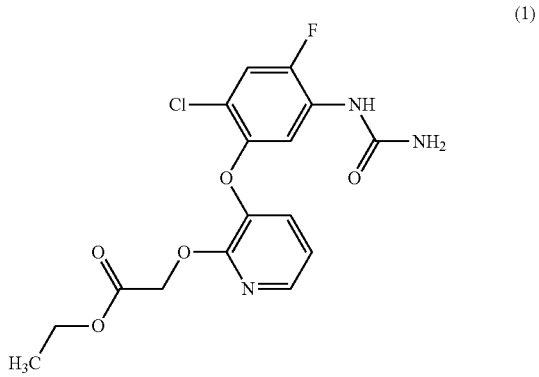 [SMILES: CCOC(=O)COc1ncccc1Oc1cc(NC(N)=O)c(F)cc1Cl]

(1)

(hereinafter, referred to as "Compound of the present invention" or "Present compound").
[2] An agent for controlling a plant disease which comprises the compound described in [1] (hereinafter, referred to as "Control agent of the present invention" or "Present control agent").
[3] A method for controlling a plant disease which comprises applying an effective amount of the compound described in [1] to a plant or soil for cultivating the plant.
[4] Use of the compound described in [1] to control a plant disease.

Effect of Invention

According to the invention, plant diseases can be controlled.

MODE FOR CARRYING OUT THE INVENTION

The control agent of the present invention is usually prepared by mixing the compound of the present invention with a solid carrier, a liquid carrier, an oil and/or a surfactant and the others, and if necessary, adding other auxiliary agents for formulation such as binders, dispersants and stabilizers and the others, to formulate into wettable powders, water-dispersible granules, flowables, granules, dry flowables, emulsifiable concentrates, aqueous solutions, oils, smoking agents, aerosols, microcapsules, and the others. Such formulations comprise usually 0.1 to 99%, preferably 0.2 to 90% by weight of the present compound.

Examples of the solid carrier include fine powders or granules of clays (for example, kaolin clay, diatomaceous earth, synthetic hydrated silicon oxides, Fubasami clay, bentonite, or acid white clay), talcs, other inorganic minerals (for example, sericite, quartz powders, sulfur powders, active carbon, calcium carbonate or hydrated silica).

Examples of the liquid carrier include water; alcohols (for example, methanol or ethanol); ketones (for example, acetone or methyl ethyl ketone); aromatic hydrocarbons (for example, toluene, xylene, ethyl benzene or methylnaphthalene); aliphatic hydrocarbons (for example, hexane, cyclohexane or kerosene); esters (for example, ethyl acetate or butyl acetate); nitriles (for example, acetonitrile or isobutyronitrile); ethers (for example, diisopropyl ether); amides (for example, dimethylformamide or dimethylacetamide); and sulfoxides (for example, dimethyl sulfoxide).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters and sugar alcohol derivatives.

Examples of the other auxiliary agents for formulation include a binder, a dispersant, and a stabilizer. Specific examples include casein, gelatin, polysaccharides (for example, starch, gum arabic, cellulose derivatives or alginic acid), lignin derivatives, bentonite, sugars, water-soluble synthetic polymers (for example, polyvinyl alcohol, polyvinyl pyrrolidone or polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), plant oil, mineral oil, fatty acid and the others.

Examples of the oils and the surfactants that may be mixed with the present compound include Nimbus (registered trademark), Assist (registered trademark), Aureo (registered trademark), Iharol (registered trademark), Silwet L-77 (registered trademark), BreakThru (registered trademark), SundanceII (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the others.

The compound of the present invention may be applied as a control agent of the present invention. Examples of a method for applying the control agent of the present invention is not limited to a specific method as long as the control agent of the present invention can be applied in a substantial applicable form, and include an application to a plant body such as a foliar application, an application to a cultivation area of plant such as a soil treatment, an application to seeds such as a seed disinfection, and the others.

The application rate of the compound of the present invention used in the control method of the present invention may be varied depending on a kind of plant to be applied, a kind and a frequency of occurrence of plant diseases to be controlled, a formulation form, a timing of application, an application method, an application site, a climate condition, and the others. For example, when the compound of the present invention is applied to stems and leaves of plants or soils for cultivating plants, the application rate of the compound of the present invention is within the range of 1 to 500 g per 1,000 m$^2$.

The emulsifiable concentrates, the wettable powders, or flowables etc. are usually applied by diluting them with water, and then spreading them. In this case, the concentration of the compound of the present invention is usually 0.0005 to 2% by weight. The dusts or the granules, etc. are usually applied as itself without diluting them.

The compound of the present invention can be used as an agent for controlling plant diseases in a farmland such as fields, paddy fields, lawns, and orchards.

Examples of the plant diseases which may be controlled by the compound of the present invention include those due to plant pathogens such as filamentous fungi and bacterium, and more specifically include the followings. The descriptions in the below-mentioned parenthesis represent a scientific name of the pathogenic fungi which causes the corresponding plant diseases.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Blumeria graminis*), fusarium Head blight (*Fusarium graminearum, F. avenaceum, F. culmorum, Microdochium nivale*), yellow rust (*Puccinia striiformis*), black rust (*Puccinia graminis*), brown rust (*Puccinia recondita*), snow mold (*Microdochium nivale, Microdochium majus*), typhula snow blight (*Typhula incarnata, Typhula ishikariensis*), loose smut (*Ustilago tritici*), stinking smut (*Tilletia caries, Tilletia controversa*), eyespot (*Pseudocercosporella herpotrichoides*), glume blotch (*Stagonospora nodorum*), tan spot (*Pyrenophora triticirepentis*), damping-off caused by rhizoctonia fungus (*Rhizoctonia solani*), and take-all disease (*Gaeumannomyces graminis*);

Barley diseases: powdery mildew (*Blumeria graminis*), fusarium head blight (*Fusarium graminearum, Fusarium avenaceum, Fusarium culmorum, Microdochium nivale*), yellow rust (*Puccinia striiformis*), black rust (*Puccinia graminis*), brown rust (*Puccinia hordei*), dwarf leaf rust (*Puccinia hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot disease (*Ramularia collocygni*), and damping-off caused by rhizoctonia fungus (*Rhizoctonia solani*);

Corn diseases: rust (*Puccinia sorghi*), southern rust (*Puccinia polysora*), northern leaf blight (*Sotosphaeria turcica*), tropical rust (*Physopella zeae*), southern leaf blight (*Cochiliobolus heterostrophus*), anthracnose (*Colletotrichum graminicola*), gray leaf spot (*Cercospora zeae-maydis*), eyespot (*Kabatiella zeae*), phaeosphaeria leaf spot disease (*Phaeosphaeria maydis*), Diplodia (*Stenocarpella maydis, Stenocarpella macrospora*), stalk rot (*Fusarium graminearum, Fusarium verticilioides, Colletotrichum graminicola*), and smut (*Ustilago maydis*);

Cotton diseases: anthracnose (*Colletotrichum gossypii*), grey mildew (*Ramularia areola*), alternaria leaf spot (*Alternaria macrospora, Alternaria gossypii*), and Black root rot caused by Thielaviopsis fungus (*Thielaviopsis basicola*);

Coffee diseases: rust (*Hemileia vastatrix*) and leaf spot (*Cercospora coffeicola*);

Rapeseed diseases: sclerotinia rot (*Sclerotinia sclerotiorum*), gray leaf spot (*Alternaria brassicae*), Phoma stem canker and Phoma leaf spot (*Phoma lingam*);

Sugarcane disease: rust (*Puccinia melanocephela, Puccinia kuehnii*);

Sunflower diseases: rust (*Puccinia helianthi*) and downy mildew (*Plasmopara halstedii*);

Citrus diseases: melanose (*Diaporthe citri*), scab (*Elsinoe fawcetti*), green mold (*Penicillium digitatum, Penicillium italicum*), and Phytophthora disease (*Phytophthora parasitica, Phytophthora citrophthora*);

Apple diseases: blossom blight (*Monilinia mali*), valsa canker (*Valsa ceratosperma*), powdery mildew (*Podosphaera leucotricha*), Alternaria leaf spot (*Alternaria alternata* apple pathotype), scab (*Venturia inaequalis*), anthracnose (*Glomerella cingulata*), blotch (*Diplocarpon mali*), ring rot (*Botryosphaeria berengeriana*), and crown rot (*Phytophthora cactorum*);

Pear diseases: scab (*Venturia nashicola, Venturia pirina*), black spot (*Alternaria alternata* Japanese pear pathotype), and rust (*Gymnosporangium haraeanum*);

Peach diseases: brown rot (*Monilinia fructicola*), scab (*Cladosporium carpophilum*), and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), corynespora leaf spot (*Corynespora cassiicola*), Fusarium wilt (*Fusarium oxysporum*), downy mildew (*Pseudoperonospora cubensis*), Phytophthora rot (*Phytophthora* sp.), and damping-off (*Pythium* sp.);

Tomato diseases: early blight (*Alternaria solani*), leaf mold (*Cladosporium fulvum*), cercospora leaf mold (*Pseudocercospora fuligena*), late blight (*Phytophthora infestans*) and powdery mildew (*Leveillula taurica*);

Eggplant disease: brown spot (*Phomopsis vexans*) and powdery mildew (*Erysiphe cichoracearum*);

Diseases of brassica family: Alternaria leaf spot (*Alternaria japonica*), white spot (*Cercosporella brassicae*), clubroot (*Plasmodiophora brassicae*), and downy mildew (*Peronospora parasitica*);

Welsh onion disease: rust (*Puccinia allii*);

Soybean diseases: Cercospora leaf blight and purple stain (*Cercospora kikuchii*), Sphaceloma scab (*Elsinoe glycines*), pod and stem blight (*Diaporthe phaseolorum* var. sojae), rust (*Phakopsora pachyrhizi*), target spot (*Corynespora cassiicola*), anthracnose (*Colletotrithum glycines, Colletotrichum truncatum*), Rhizoctonia rot (*Rhizoctonia solani*), septoria brown spot (*Septoria glycines*), frog eye leaf spot (*Cercospora sojina*), stem rot (*Sclerotinia sclerotiorum*), powdery mildew (*Microsphaera diffusa*), phytophthora root and stem rot (*Phytophthora sojae*), downy mildew (*Peronospora manshurica*), and sudden death syndrome (*Fusarium virguliforme*);

Kidney bean diseases: stem rot (*Sclerotinia sclerotiorum*), rust (*Uromyces appendiculatus*), angular leaf spot (*Phaeoisariopsis griseola*), and anthracnose (*Colletotrichum lindemuthianum*);

Peanut diseases: leaf spot (*Cercospora personata*), brown leaf spot (*Cercospora arachidicola*), and southern blight (*Sclerotium rolfsii*);

Garden pea disease: powdery mildew (*Erysiphe pisi*);

Potato diseases: early blight (*Alternaria solani*), late blight (*Phytophthora infestans*), pink rot (*Phytophthora erythroseptica*), powdery scab (*Spongospora subterranea f. sp. subterranea*), and Verticillium wilt (*Verticillium alboatrum, Verticillium dahliae, Verticillium nigrescens*);

Strawberry disease: powdery mildew (*Sphaerotheca humuli*);

Tea diseases: net blister blight (*Exobasidium reticulatum*), white scab (*Elsinoe leucospila*), gray blight (*Pestalotiopsis* sp.), and anthracnose (*Colletotrichum theae sinensis*);

Tabacco diseases: brown spot (*Alternaria longipes*), anthracnose (*Colletotrichum tabacum*), downy mildew (*Peronospora tabacina*), and black shank (*Phytophthora nicotianae*);

Sugar beet diseases: cercospora leaf spot (*Cercospora beticoa*), leaf blight (*Thanatephorus cucumeris*), root rot (*Thanatephorus cucumeris*), and aphanomyces root rot (*Aphanomyces cochlioides*), rust (*Uromyces betae*);

Rose diseases: black spot (*Diplocarpon rosae*) and powdery mildew (*Sphaerotheca pannosa*);

Chrysanthemun diseases: leaf blight (*Septoria chrysanthemi-indici*) and white rust (*Puccinia horiana*);

Onion diseases: Botrytis leaf blight (*Botrytis cinerea, B. byssoidea, B. squamosa*), gray-mold neck rot (*Botrytis alli*), and snail sclerotial (*Botrytis squamosa*);

Various crops disease: Sclerotinia rot (*Sclerotinia sclerotiorum*);

Japanese radish disease: Alternaria leaf spot (*Alternaria brassicicola*);

Turfgrass diseases: dollar spot (*Sclerotinia homoeocarpa*), and brown patch and large patch (*Rhizoctonia solani*);

Banana disease: Sigatoka disease (*Mycosphaerella fijiensis, Mycosphaerella musicola*);

Seed diseases or diseases in the early stages of the growth of various crops caused by fungi from genera of *Aspergillus, Penicillium, Fusarium, Gibberella, Tricoderma, Thielaviopsis, Rhizopus, Mucor, Corticium, Phoma, Rhizoctonia, Diplodia*, and the others;

Viral diseases of various crops mediated by genera of *Polymyxa, Olpidium*, or the others; and rice damping-off (*Burkholderia plantarii*);

cucumber phytophthora blight (*Phytophthora capsici*), damping-off (*Pythium ultimum*) and cucumber bacterial spot (*Pseudomonas syringae* pv. *Lachrymans*);

eggplant bacterial wilt (*Ralstonia solanacearum*);

citrus canker (*Xanthomonas citri*);

Chinese cabbage slimy soft rot (*Erwinia carotovora*); and the others.

EXAMPLES

Hereinafter, the present invention is explained in more detail by using Preparation example and Test example, however, the present invention should not be limited to these examples.

First, the Preparation example is shown.

Preparation Example

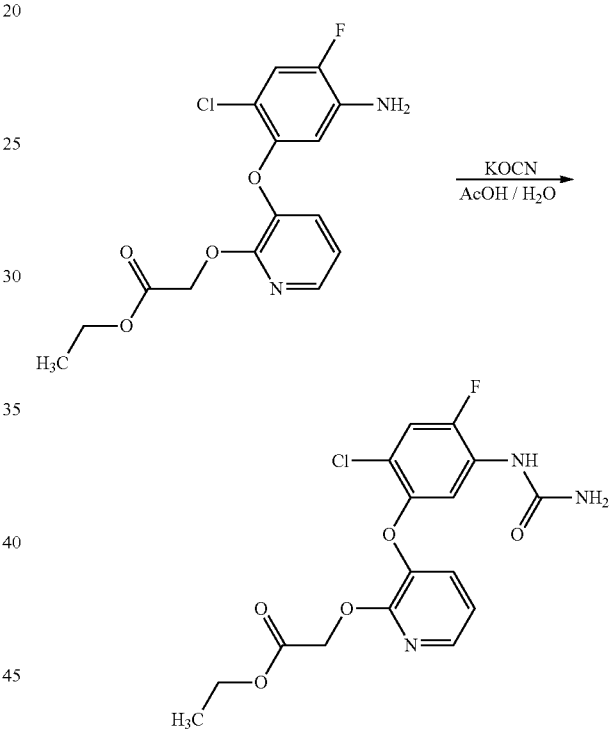

One point two (1.20) grams of 4-Chloro-2-fluoro-5-(2-(ethoxycarbonyl)methoxy-3-pyridyloxy)aniline was added to a mixture of 18 ml of acetic acid and 2.7 ml of water at room temperature, followed by adding 572 mg of Potassium cyanate 572 mg thereto. The mixture was stirred at room temperature for 2 hours, and then the resulting mixture was concentrated under reduced pressure. The resulting residues were subjected to a silica gel column chromatography to give 1.10 g of the Present compound.

$^1$H-NMR (DMSO-D$_6$) δ (ppm): 8.56 (1H, d, J=2.0 Hz), 7.91 (1H, d, J=7.7 Hz), 7.87 (1H, dd, J=5.0, 1.4 Hz), 7.56 (1H, d, J=10.9 Hz), 7.21 (1H, dd, J=7.9, 1.4 Hz), 6.99 (1H, dd, J=7.9, 5.0 Hz), 6.24 (2H, s), 4.93 (2H, s), 4.10 (2H, q, J=7.1 Hz), 1.15 (3H, t, J=7.1 Hz).

Next, the rest example is shown.

Test example 1: Test for controlling cucumber phytophthora blight fungi (*Phytophthora capsici*)

Four point five (4.5) milligrams of the present compound was diluted with 100 μL of dimethyl sulfoxide. One (1) μL portion of the diluted liquid was dispensed into a titer plate (96 wells), and thereto was then dispensed 150 μL of a potato dextrose broth medium (PDB medium) containing zoospores of cucumber phytophthora blight fungi (*Phytophthora capsici*). This plate was cultured at 27° C. for three days, thereby allowing the cucumber phytophthora blight fungi to undergo proliferation, and the absorbance at 600 nm of each well of the titer plate was then measured to determine a degree of growth of the cucumber phytophthora blight fungi. The efficacy was calculated from the determined degree of growth by the below-mentioned "Equation 1". As a result, the efficacy of the Present compound was 90% or more.

Efficacy=100×(X−Y)/X     "Equation 1"

where
X: Degree of fungal growth in non-treated area
Y: Degree of fungal growth in treated area In the test example, a non-treated area means an area in which a test was conducted in the same manner, except that dimethyl sulfoxide was dispensed in place of the present compound diluted with dimethyl sulfoxide.

Whilst, the similar test was conducted by using N-[4-chloro-2-fluoro-5-{2-(ethoxycarbonyl)methoxy-3-pyridyloxy}phenyl]acetamide which is described in EP patent No. 1122244 B2 instead of the present compound, and the efficacy thereof was less than 50%.

INDUSTRIAL APPLICABILITY

The compound of the present invention has efficacies for controlling plant diseases, and is useful as an active ingredient for an agent for controlling plant diseases.

The invention claimed is:

1. A compound represented by formula (1):

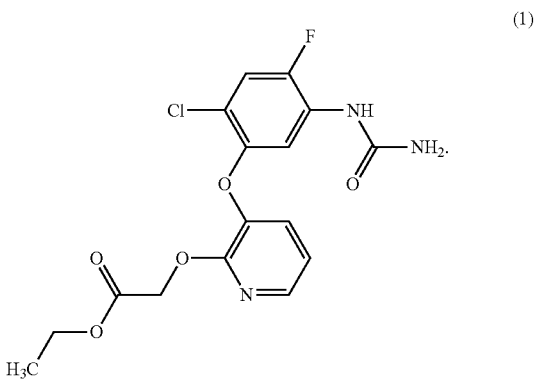 [SMILES: CCOC(=O)COc1ncccc1Oc1cc(NC(N)=O)c(F)cc1Cl]

2. An agent for controlling a plant disease which comprises the compound according to claim 1.

3. A method for controlling a plant disease which comprises applying an effective amount of the compound according to claim 1 to a plant or soil for cultivating the plant.

* * * * *